United States Patent
Ueki et al.

(10) Patent No.: US 6,673,368 B2
(45) Date of Patent: Jan. 6, 2004

(54) COLONIC MOTOR DYSFUNCTION REMEDIES COMPRISING AMINOTHIAZOLE DERIVATIVES AS ACTIVE INGREDIENTS

(75) Inventors: Shigeru Ueki, Konan-machi (JP); Yuko Hori, Konan-machi (JP); Yugo Matsunaga, Konan-machi (JP); Masaaki Nagasawa, Konan-machi (JP); Hiroyasu Nishioka, Konan-machi (JP); Masakazu Murata, Konan-machi (JP)

(73) Assignee: Zeria Phamaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/853,746

(22) Filed: May 14, 2001

(65) Prior Publication Data

US 2002/0051805 A1 May 2, 2002

(30) Foreign Application Priority Data

Sep. 8, 2000 (JP) ........................................ 2000-273025

(51) Int. Cl.$^7$ ............................................. A61K 31/36
(52) U.S. Cl. ................... 424/464; 424/451; 424/485; 514/365; 514/370; 548/195; 548/122
(58) Field of Search .................. 514/365, 370; 548/195, 122; 424/464, 451, 489

(56) References Cited

U.S. PATENT DOCUMENTS

| | | | | |
|---|---|---|---|---|
| 5,574,054 A | 11/1996 | Kitagawa et al. | ............ | 514/365 |
| 5,981,557 A | 11/1999 | Nagasawa et al. | ........... | 514/365 |
| 6,121,301 A | 9/2000 | Nagasawa et al. | ........... | 514/365 |
| 6,197,970 B1 | 3/2001 | Nagasawa et al. | ........... | 548/195 |

FOREIGN PATENT DOCUMENTS

| | | | |
|---|---|---|---|
| EP | 870 765 | * | 10/1998 |
| EP | 934938 | * | 8/1999 |
| WO | WO 96/36619 | | 11/1996 |
| WO | WO 98/17654 | | 4/1998 |
| WO | WO 98/58918 | | 12/1998 |

OTHER PUBLICATIONS

Yukiko Mine, et al., The Journal of Pharmacology and Experimental Therapeutics, "Comparison of Effect of Mosapride Citrate and Existing 5–HT$_4$ Receptor Agonists on Gastrointestinal Motility In Vivo and In Vitro," vol. 283, No. 3, (1997), pp. 1000–1008.
C. Roman, et al., Physiologoy of the Gastrointestinal Tract, "Extrinsic Control of Digestive Tract Motility," Second Edition, Chapter 15, (1987), pp. 507, 523 and 536.
J.A. Ritchie, Gut, "Colonic Motor Activity and Bowel Function," (1968), pp. 442–456.
G. Noll, et al., Cardilogy, vol. 89 (suppl. 1), pp. 10–15, "Comparative Pharmacological Properties Among Calcium Channel Blockers: T–Channel Versus L–Channel Blockade", 1998.
C. De Montigny, et al., Journal of Clinical Psychopharmacology, vol. 19, No. 5, pp. 401–406, "Venlafaxine in Treatment–Resistant Major Depression: A Canadian Multicenter, Open–Label Trial", 1999.
M. W. Jann, Pharmacotherapy, vol. 11, No. 3, pp. 179–195, "Evaluations of New Drugs", 1991.
J. E. Pandolfino, et al., Gastroenterology, vol. 118, No. 2, pp. S32–S47, "Motility–Modifying Agents and Management of Disorders of Gastrointestinal Motility", 2000.
F. Lechin, et al., The Journal of Clinical Pharmacology, vol. 19, pp. 617–625, "Effects of Dopaminergic Blocking Agents on Distal Colon Motility", Oct. 1979.
P. G. Farup, et al., Scand. J. Gastroenterol., vol. 33, pp. 128–131, "The Symptomatic Effect of Cisapride in Patients with Irritable Bowel Syndrome and Constipation", 1998.
K. Schuetze, et al., Aliment Pharmacol Ther, vol. 11, pp. 387–394, "Double–Blind Study of the Effect of Cisapride on Constipation and Abdominal Discomfort as Components of the Irritable Bowel Syndrome", 1997.

* cited by examiner

*Primary Examiner*—Thurman K. Page
*Assistant Examiner*—Lakshmi Channavajjala
(74) *Attorney, Agent, or Firm*—Oblon, Spivak, McClelland, Maier & Neustadt, P.C.

(57) ABSTRACT

Remedies effective for the improvement of colonic motor dysfunction such as irritable bowel syndrome, constipation or intestinal atony without causing side effects on the central nerve system. These colonic motor dysfunction remedies comprise, as active ingredients, aminothiazole derivatives represented by the following formula (I) or a salt or hydrate thereof:

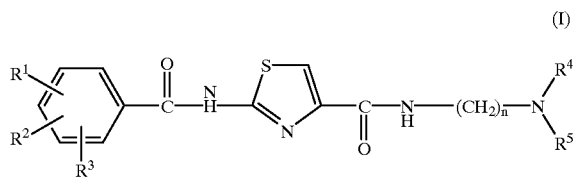

wherein $R^1$, $R^2$ and $R^3$ may be the same or different and each independently represent a hydrogen atom or a hydroxyl, lower alkyl, lower alkoxy, amino, nitro or cyano group, $R^4$ and $R^5$ may be the same or different and each independently represent a hydrogen atom or a lower alkyl group, and n stands for an integer of from 2 to 4.

32 Claims, No Drawings

COLONIC MOTOR DYSFUNCTION REMEDIES COMPRISING AMINOTHIAZOLE DERIVATIVES AS ACTIVE INGREDIENTS

TECHNICAL FIELD

This invention relates to remedies for colonic motor dysfunction, and more specifically to colonic motor dysfunction remedies comprising aminothiazole derivatives as active ingredients. This invention is also concerned with a treatment method for colonic motor dysfunction.

BACKGROUND ART

From the anatomical viewpoint, the digestive tract is divided roughly into an upper digestive tract and a lower digestive tract. The upper digestive tract includes the esoplagus, the stomach and the duodenum, while the lower digestive tract includes the small intestine, the large intestine and the rectal. To diseases and symptoms which occur in the respective regions, treatments are applied correspondingly.

Illustrative of diseases of the upper digestive tract are diseases in the esophageal region, such as esophageal carcinoma, esophagostenosis and reflux esophagitis; diseases in the gastric region, such as gastric ulcer, gastritis and gastric cancer; diseases in the duodenal region, such as duodenal ulcer and duodenal cancer; and as diseases occurring commonly in the gastric region and duodenal region, NUD (Non-Ulcer Dyspepsia) and gastroduodenal motor dysfunction. Examples of symptoms of such diseases of the upper digestive tract with which gastroduodenal motor dysfunction is associated include epigastric malaise, nausea, vomitting, brash, anorexia, bellyache, and dilatation of the stomach.

Illustrative of diseases of the lower digestive tract are colon cancer, colon polyp, ulcerative collitis, Crohn's disease, irritable bowel syndromes, constipation, intestinal atony, and drug-induced motor dysfunction. Of these, irritable bowel syndromes, constipation, intestinal atony and drug-induced motor dysfunction are diseases attributable to motor dysfunction of the large intestine, and are known to develop a cathartic disorder, such as constipation or diarrhea, and/or bellyache. Drug-induced motor dysfunction, on the other hand, is known to occur as a result of use of a calcium antagonist, a psychotropic or an antidepressant [Cardiology, 89(suppl. 1), 10–15, 1998; J. Clin. Psychopharmacol., 19, 401–406, 1999; Pharmacotherapy, 11, 179–195, 1991].

As improvers for irritable bowel syndromes, trimebutine maleate, allosetron hydrochloride and tegaseroid maleate are known. Of these, trimebutine maleate has been found to give side effects on the central nerve system (sleep, dizziness and the like) via opioid receptors. With respect to allosetron hydrochloride and tegaseroid maleate which are effective for diarrheal IBS and constipated IBS, respectively, there is an outstanding concern about side effect of constipation as an excess effect because drug efficacy is developed via serotonin receptors.

As gastroprokinetic agents for the upper digestive tract, cisapride, metoclopramide, itopride hydrochloride, mosapride citrate and the like are known (Gastroenterology, 118, S32–S47, 2000). However, these improvers have been reported to be ineffective for constipation associated with irritable bowel syndromes which are diseases caused by colonic motor dysfunction (J. Clin. Pharmacol., 19, 617–625, 1979; Scand. J. Gastroenterol., 33, 128–131, 1998;Aliment. Pharmacol. Ther., 11, 387–394, 1997).

PCT International Publications WO96/36619 and WO98/17654 disclose that aminothiazole derivatives enhance gastric motor activity and improve epigastric malaise, nausea, vomitting, brash, anorexia, bellyache, and dilatation of the stomach. These publications, however, make no mention about improving effects on diseases of the lower digestive tract caused by colonic motor dysfunction.

There is, accordingly, an outstanding desire for the development of improvers for colonic motor dysfunction, which are free of such side effects as those observed on the conventional irritable bowel syndrome improvers and caused via opioid receptors or serotonin receptors.

DISCLOSURE OF THE INVENTION

The present invention provides a colonic motor dysfunction remedy comprising, as an active ingredient, an aminothiazole derivative represented by the following formula (I) or a salt or hydrate thereof:

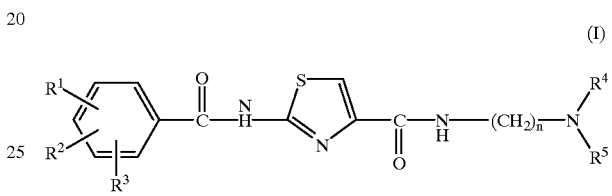

wherein $R^1$, $R^2$ and $R^3$ may be the same or different and each independently represent a hydrogen atom or a hydroxyl, lower alkyl, lower alkoxy, amino, nitro or cyano group, $R^4$ and $R^5$ may be the same or different and each independently represent a hydrogen atom or a lower alkyl group, and n stands for an integer of from 2 to 4.

The present invention also provides use of an aminothiazole derivative represented by the formula (I) or a salt or hydrate thereof for the production of a colonic motor dysfunction remedy.

The present invention also provides a treatment method for colonic motor dysfunction, which comprises administering an effective amount of an aminothiazole derivative represented by the formula (I) or a salt or hydrate thereof.

BEST MODES FOR CARRYING OUT THE INVENTION

In the aminothiazole derivative (I) useful in the practice of the present invention, the term "lower alkyl" means a linear, branched or cyclic, saturated hydrocarbon group which preferably has 1 to 6 carbon atoms. On the other hand, the term "lower alkoxy" means a group formed of a linear, branched or cyclic, saturated hydrocarbon, which preferably has 1 to 6 carbon atoms, and an oxygen atom bonded to the hydrocarbon.

Accordingly, illustrative of the "lower alkyl group" as $R^1$, $R^2$, $R^3$, $R^4$ and $R^5$ are linear, branched or cyclic alkyl groups having 1 to 6 carbon atoms, such as methyl, ethyl, propyl, isopropyl, cyclopropyl, butyl, isobutyl, sec-butyl, tert-butyl, cyclobutyl, pentyl, 1-methylbutyl, 2-methylbutyl, isopentyl, tert-pentyl, 1,2-dimethylpropyl, neopentyl, 1-ethylpropyl, cyclopentyl, hexyl, 1-methylpentyl, 2-methyl-pentyl, 3-methylpentyl, isohexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methyl-1-ethylpropyl, 1-ethyl-2-methylpropyl, 1,1,2-trimethylpropyl, 1,2,2-trimethylpropyl, and cyclohexyl. Among these, more preferred lower alkyl groups are linear or branched alkyl groups having 1 to 4 carbon atoms.

Particularly preferred as $R^4$ and $R^5$ is isopropyl. Particularly preferred as $R^1$, $R^2$ and $R^3$ are H, hydroxy, methoxy, amino, nitro and cyano.

Illustrative of the "lower alkoxy group" as $R^1$, $R^2$ and $R^3$ are linear, branched or cyclic alkoxy groups having 1 to 6 carbon atoms, such as methoxy, ethoxy, propoxy, isopropoxy, cyclopropoxy, butoxy, isobutoxy, sec-butoxy, tert-butoxy, cyclobutoxy, pentoxy, 1-methylbutoxy, 2-methylbutoxy, isopentoxy, tert-pentoxy, 1,2-dimethylpropoxy, neopentoxy, 1-ethylpropoxy, cyclopentoxy, hexyloxy, 1-methylpentoxy, 2-methylpentoxy, 3-methylpentoxy, isohexyloxy, 1-ethylbutoxy, 2-ethylbutoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-methyl-1-ethylpropoxy, 1-ethyl-2-methylpropoxy, 1,1,2-trimethylpropoxy, 1,2,2-trimethyl-propoxy, and cyclohexyloxy. Among these, more preferred lower alkoxy groups are linear or branched alkoxy groups having 1 to 4 carbon atoms. Particularly preferred is methoxy.

As n, 2 is particularly preferred.

Preferred examples of the aminothiazole derivative (I) useful in the practice of the present invention can include compounds in which $R^1$, $R^2$ and $R^3$ are the same or different and each independently represent a hydroxyl group or a linear, branched or cyclic alkoxy group having 1 to 6 carbon atoms, specifically a methoxy group or one of $R^1$, $R^2$ and $R^3$ is an amino, nitro or cyano group and the remaining two substituents are hydrogen atoms; $R^4$ and $R^5$ are the same and each represent an alkyl group having 1 to 6 carbon atoms, specifically an isopropyl group; and n is 2. Illustrative of particularly preferred compounds are
N-(N',N'-diisopropylaminoethyl)-[2-(2-hydroxy-4,5-dimethoxy benzoylamino)-1,3-thiazol-4-yl] carboxamide,
N-(N',N'-diisopropylaminoethyl)-[2-(3-cyano-benzoylamino)-1,3-thiazol-4-yl]carboxamide, and
N-(N',N'-diisopropylaminoethyl)-[2-(3-aminobenzoylamino)-1,3-thiazol-4-yl]carboxamide.

Examples of the salt of the aminothiazole derivative (I), which is also useful in the practice of the present invention, can include inorganic acid addition salts, such as the hydrochloride, sulfate, nitrate, phosphate, hydrobromide and hydroiodide; and organic acid addition salts, such as the acetate, oxalate, malonate, succinate, maleate, fumarate, lactate, malate, citrate, tartrate, methanesulfonate and ethansulfonate. A preferred example of the salt is the hydrochloride.

The aminothiazole derivative (I) useful in the practice of the present invention includes various solvates such as hydrate.

The aminothiazole derivative (I) useful in the practice of the present invention can be prepared by the process disclosed in PCT International Publication WO96/36619 or WO98/17654.

In the present invention, the aminothiazole derivative (I) can be formulated together with a pharmaceutically acceptable carrier into a composition for oral administration or parenteral administration. As compositions for oral administration, the aminothiazole derivative (I) useful in the practice of the present invention can be formulated into tablets, powder, granules or capsules by using suitable additives, for example, an excipient such as lactose, mannitol, corn starch or crystalline cellulose; a binder such as a cellulose derivative, gum arabic or gelatin; a disintegrator such as carboxy-methylcellulose calcium; a lubricant such as talc or magnesium stearate; and the like. Further, these solid preparations can be formed into enteric preparations by using a coating base such as hydroxypropyl methylcellulose phthalate, hydroxypropyl methylcellulose acetate succinate, cellulose acetate phthalate or a methacrylate copolymer. As compositions for parenteral administration, the aminothiazole derivative (I) useful in the practice of the present invention can be formulated into liquid preparations for injection, for example, by making combined use of water, ethanol, glycerin, a commonly employed surfactant and the like, or into suppositories by using a suppository base.

In the present invention, the dosage of the aminothiazole derivative (I) may range generally from 0.1 to 2,000 mg/day, preferably from 1 to 300 mg/day, notably from to mg/day in the case of oral administration although it varies depending on the age, weight, symptom, effects of treatment, administration method, and administration period. It is preferred to administer this dosage in a range of from 1 to 3 times a day.

As the aminothiazole derivative (I) useful in the practice of the present invention have excellent colomotor enhancing effect and high safety as will be described subsequently herein, it is useful as a remedy for colonic motor dysfunction of mammals including human being. Illustrative of colonic motor dysfunction are irritable bowel syndrome, constipation, intestinal atony, and drug-induced motor dysfunction. It does not act on serotonin receptors or dopamine receptors [Gastroenterology, 116(4) part 2, A1094, 1999] and different from conventional drugs, do not have side effects such as side effects on the central nerve system, e.g., extrapyramidal disorders and dizziness, and constipation as an excess effect.

EXAMPLES

The present invention will hereinafter be described in detail based on Examples. It should, however, be borne in mind that the present invention is not limited to the Examples.

[Pharmacological Test]

A description will next be made about a pharmacological test on certain aminothiazole derivatives (I) useful in the practice of the present invention. The followings are the compounds (test compounds) which were employed as test drugs:

(Compound 1)

N-(N',N'-diisopropylaminoethyl)-[2-(2-hydroxy-4,5-dim ethoxybenzoylamino)-1,3-thiazol-4-yl]carboxamide HCL trihydrate [Synthesized in accordance with the procedures of Example 38 of WO96/36619.]

(Compound 2)

N-(N',N'-diisopropylaminoethyl)-[2-(3-cyanobenzoyl-am ino)-1,3-thiazol-4-yl]carboxamide hydrochloride [Synthesized in accordance with the procedures of Example 1 of WO98/17654.]

(Compound 3)

N-(N',N'-diisopropylaminoethyl)-[2-(3-aminobenzoyl-am ino)-1,3-thiazol-4-yl]carboxamide [Synthesized in accordance with the procedures of Example 157 of WO96/36619.]

Test 1 [Effects on Gastric and Colonic Motor Activity]

Force transducers ("F-12IS", trade name; manufactured by Star Medical Technologies, Inc.) were chronically sutured in the gastric antrum and large intestines of male dogs (body weight: 9 to 11 kg, 5 to 6 dogs per group) (Itoh, Z. et al., Am. J. Dig. Dis. 22, 117–124, 1977). Contraction signals from the respective regions in postcibal period were amplified and recorded ("RTA-1200", trade name; manufactured by Nihon Kohden Corporation). The contraction signals, which had been collected in a computer, were analyzed by using an analysis program ("DSSDDWHD V.30", trade name; prepared by Nihon Kohden Corporation), whereby motor indexes were calculated. The test drugs were administered through catheters which had been chronically indwelled beforehand in the duodenum, respectively. Supposing that the coefficient of motor 30 minutes before the administration of drug was 100%, the results were calculated as percents of motor index until 1 hour after the administration. The results are presented in Table 1.

TABLE 1

Effects on Gastric and Colonic Motor Activity

| | | Percent of motor index | |
|---|---|---|---|
| Test drug | Dosage (mg/kg) | Gastric antrum | Large intestine |
| Control | — | 91.3 | 93.1 |
| Compound 1 | 10 | 163.7 | 136.1 |
| Compound 2 | 10 | 189.5 | 221.7 |
| Compound 3 | 10 | 244.6 | 249.9 |
| Cisapride | 1 | 158.7 | 114.5 |
| Itopride | 10 | 132.7 | 122.1 |
| Mosapride | 3 | 146.2 | 119.2 |

As is evident from Table 1, all the test drugs showed gastroprokinetic activity, but concerning colonic motility, cisapride, itopride and mosapride which are conventional drugs showed no significant effect whereas Compounds 1 to 3 which are compounds useful in the practice of the present invention exhibited marked enhancement of colonic motor activity.

Test 2 [Effects on Defecation]

Test drugs were intraperitoneally administered to male SD rats (8 rats per group). Stools were recovered until 60 minutes after the administration, and their dry weights were measured. Supposing that that the average of stool weights in a control group was 100%, the averages of percent weights of individual test drug groups were calculated. The results are presented in Table 2.

TABLE 2

Effects on Defecation in Rats

| Test drug | Dose (mg/kg) | Percent stool weight (%) |
|---|---|---|
| Control | — | 105.6 |
| Compound 1 | 10 | 361.8 |
| Compound 2 | 10 | 766.7 |
| Compound 3 | 10 | 733.3 |

As is apparent from Table 2, all the test drugs of Compounds 1 to 3 were confirmed to bring about a marked increase in stool weight. Incidentally, the conditions of those stools were all normal.

[Acute Toxicity Test]

ICR mice of 4 to 5 weeks old were used in groups, each consisting of 3 mice. The individual test compounds were separately suspended in a 0.5% methylcellulose solution and orally administered at 1,000 mg/kg, and the mice were observed for 1 week. No case of death was observed in any of the groups administered with Compounds 1 to 3, respectively.

Preparation Example 1

| Compound 1 | 20 g |
|---|---|
| Lactose | 315 g |
| Corn starch | 125 g |
| Crystalline cellulose | 25 g |

The above-described ingredients were combined into an intimate mixture, followed by the addition of a 7.5% aqueous solution of hydroxypropylcellulose (200 mL). The resulting mixture was formed into green granules through a screening of 0.5 mm in diameter. After the green granules were immediately rounded in a Marumerizer, they were dried into granules.

Preparation Example 2

| Compound 2 | 20 g |
|---|---|
| Lactose | 100 g |
| Corn starch | 36 g |
| Crystalline cellulose | 30 g |
| Carboxymethylcellulose calcium | 10 g |
| Magnesium stearate | 4 g |

The above-described ingredients were combined into an intimate mixture. The mixture was formed into tablets of 200 mg/tablet by a punch of 7.5 mm in diameter by a single-punch tableting machine.

Preparation Example 3

| Compound 1 | 100 mg |
|---|---|
| Sodium acetate | 2 mg |
| Acetic acid | q.s. to pH 5.8 |
| Distilled water | q.s. to 10 mL |
| Total: | 10 mL/vial |

In accordance with the above formula, an injection was prepared in a manner known per se in the art.

INDUSTRIAL APPLICABILITY

The aminothiazole derivative (I) useful in the practice of the present invention has excellent effect for improving colonic motor dysfunction and moreover, do not give side effect on the central nerve system via serotonin receptors or dopamine receptors. It is, therefore, useful as a remedy for irritable bowel syndrome, constipation, intestinal atony, drug-induced colonic motor dysfunction or the like.

What is claimed is:

1. A method of treating colonic motor dysfunction, which comprises administering an effective amount of an aminothiazole derivative represented by the following formula (I) or a salt or hydrate thereof:

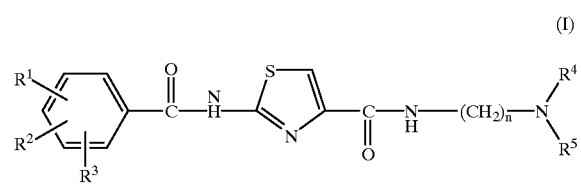

(I)

wherein $R^1$, $R^2$ and $R^3$ may be the same or different and each independently represent a hydrogen atom or a hydroxyl, lower alkyl, lower alkoxy, amino, nitro or cyano group, $R^4$ and may be the same or different and each independently represent a hydrogen atom or a lower alkyl group, and n stands for an integer of from 2 to 4.

2. The method according to claim 1, wherein in the formula (I), said lower alkyl group is a linear, branched or cyclic alkyl group having 1 to 6 carbon atoms, and said lower alkoxy group is a linear, branched or cyclic alkoxy group having 1 to 6 carbon atoms.

3. The method according to claim 1, wherein in the formula (I), wherein $R^1$, $R^2$ and $R^3$ may be the same or different and each independently represent a hydroxyl group or an alkoxy group having 1 to 6 carbon atoms, $R^4$ and $R^5$ are the same and each represent an alkyl group having 1 to 6 carbon atoms, and n is 2.

4. The method according to claim 1, wherein in the formula (I), one of $R^1$, $R^2$ and $R^3$ is an amino, nitro or cyano group and each of the remaining two substituents is a hydrogen atom, $R^4$ and $R^5$ are the same and each represent an alkyl group having 1 to 6 carbon atoms, and n is 2.

5. The method according to claim 1, which comprises as an active ingredient
N-(N',N'-diisopropylaminoethyl)-[2-(2-hydroxy-4,5-dimethoxy benzoylamino)-1,3-thiazol-4-yl] carboxamide or a salt or hydrate thereof.

6. The method according to claim 1, which comprises as an active ingredient
N-(N',N'-diisopropylaminoethyl)-[2-(3-cyanobenzoylamino)-1,3-thiazol-4-yl]carboxamide or a salt or hydrate thereof.

7. The method according to claim 1, which comprises as an active ingredient
N-(N',N'-diisopropylaminoethyl)-[2-(3-aminobenzoylamino)-1,3-thiazol-4-yl]carboxamide or a salt or hydrate thereof.

8. The method according to claim 1, wherein said colonic motor dysfunction is irritable bowel syndrome, constipation, intestinal atony or drug-induced colonic motor dysfunction.

9. The method according to claim 1, wherein said aminothiazole derivative is orally administered at a dosage of 0.1 to 2,000 mg/day.

10. The method according to claim 1, wherein said colonic motor dysfunction is colon cancer, colon polyp, ulcerative collitis, and Crohn's disease.

11. The method according to claim 1, wherein said colonic motor dysfunction is irritable bowel syndrome.

12. The method according to claim 1, wherein said colonic motor dysfunction is constipation.

13. The method according to claim 1, wherein said colonic motor dysfunction is intestinal atony.

14. The method according to claim 1, wherein said colonic motor dysfunction is drug-induced colonic motor dysfunction.

15. The method according to claim 2, wherein said colonic motor dysfunction is irritable bowel syndrome, constipation, intestinal atony or drug-induced colonic motor dysfunction.

16. The method according to claim 3, wherein said colonic motor dysfunction is irritable bowel syndrome, constipation, intestinal atony or drug-induced colonic motor dysfunction.

17. The method according to claim 4, wherein said colonic motor dysfunction is irritable bowel syndrome, constipation, intestinal atony or drug-induced colonic motor dysfunction.

18. The method according to claim 5, wherein said colonic motor dysfunction is irritable bowel syndrome, constipation, intestinal atony or drug-induced colonic motor dysfunction.

19. The method according to claim 6, wherein said colonic motor dysfunction is irritable bowel syndrome, constipation, intestinal atony or drug-induced colonic motor dysfunction.

20. The method according to claim 7, wherein said colonic motor dysfunction is irritable bowel syndrome, constipation, intestinal atony or drug-induced colonic motor dysfunction.

21. The method according to claim 2, wherein said aminothiazole derivative is orally administered at a dosage of 0.1 to 2,000 mg/day.

22. The method according to claim 3, wherein said aminothiazole derivative is orally administered at a dosage of 0.1 to 2,000 mg/day.

23. The method according to claim 4, wherein said aminothiazole derivative is orally administered at a dosage of 0.1 to 2,000 mg/day.

24. The method according to claim 5, wherein said aminothiazole derivative is orally administered at a dosage of 0.1 to 2,000 mg/day.

25. The method according to claim 6, wherein said aminothiazole derivative is orally administered at a dosage of 0.1 to 2,000 mg/day.

26. The method according to claim 7, wherein said aminothiazole derivative is orally administered at a dosage of 0.1 to 2,000 mg/day.

27. A method of treating the symptoms of colonic motor dysfunction, which comprises administering an effective amount of an aminothiazole derivative represented by the following formula (I) or a salt or hydrate thereof:

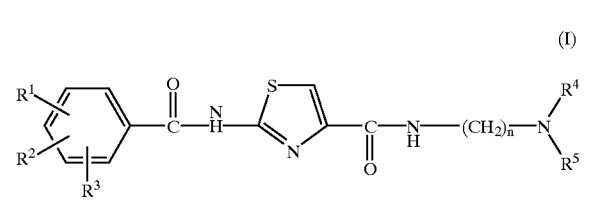

(I)

wherein $R^1$, $R^2$ and $R^3$ may be the same or different and each independently represent a hydrogen atom or a hydroxyl, lower alkyl, lower alkoxy, amino, nitro or cyano group, $R^4$ and may be the same or different and each independently represent a hydrogen atom or a lower alkyl group, and n stands for an integer of from 2 to 4.

28. The method according to claim 27, wherein said colonic motor dysfunction is colon cancer, colon polyp, ulcerative collitis, and Crohn's disease.

29. The method according to claim 27, wherein said colonic motor dysfunction is irritable bowel syndrome.

30. The method according to claim 27, wherein said colonic motor dysfunction is constipation.

31. The method according to claim 27, wherein said colonic motor dysfunction is intestinal atony.

32. The method according to claim 27, wherein said colonic motor dysfunction is drug-induced colonic motor dysfunction.

* * * * *